United States Patent [19]

Garland et al.

[11] Patent Number: 5,055,582

[45] Date of Patent: Oct. 8, 1991

[54] PROCESS FOR PREPARING THROMBOXANE $A_2$ ANTAGONISTS

[75] Inventors: Robert B. Garland; Masateru Miyano, both of Northbrook, Ill.

[73] Assignee: National Research Development Corporation, London, England

[21] Appl. No.: 283,639

[22] Filed: Dec. 13, 1988

[51] Int. Cl.$^5$ .................. C07D 413/02; C07D 413/14; C07D 211/68; C07D 211/80; C07D 277/62; C07D 277/68; C07D 277/82; C07D 263/60; C07C 321/02; C07C 323/02; C07C 325/02; C07C 323/10; C07C 273/00; C07C 273/02; C07C 275/02; C07C 275/06

[52] U.S. Cl. .................................. 546/256; 546/257; 546/258; 546/261; 546/264; 546/265; 546/269; 546/267; 546/270; 546/285; 546/291; 546/293; 546/294; 546/295; 546/296; 546/297; 546/300; 546/305; 546/306; 546/307; 546/308; 546/309; 546/311; 546/312; 546/331; 546/332; 546/333; 546/334; 546/335; 546/337; 560/9; 560/10; 560/20; 560/21; 560/22; 560/23; 560/12; 560/13; 560/35; 562/426; 562/427; 562/429; 562/430; 562/434; 562/435; 562/437; 562/438; 562/439; 562/440; 564/17; 564/26; 564/27; 564/47; 564/48; 564/49; 564/50; 564/51; 564/52; 564/53; 564/54; 564/56; 564/57; 564/102; 564/154; 564/161; 564/162; 564/163; 564/164; 564/165; 564/166; 564/167; 548/156; 548/157; 548/159; 548/160; 548/161; 548/164; 548/165; 548/166; 548/167; 548/170; 548/171; 548/178; 548/180; 548/217; 548/219; 548/221; 548/220; 548/222; 548/224; 549/283; 549/290

[58] Field of Search .............. 546/256, 257, 258, 261, 546/264, 265, 269, 267, 270, 285, 291, 293, 294, 295, 296, 297, 300, 305, 306, 307, 309, 311, 312, 331, 332, 333, 334, 335, 337; 548/156, 157, 159, 160, 161, 164, 165, 166, 167, 170, 171, 178, 180, 217, 219, 221, 222, 224, 220; 560/9, 10, 20, 21, 22, 23, 12, 13, 35; 562/426, 427, 429, 430, 434, 435, 437, 438, 439, 440; 564/17, 26, 27, 47, 48, 49, 50, 51, 52, 53, 54, 56, 57, 102

[56] References Cited

U.S. PATENT DOCUMENTS

| | | | |
|---|---|---|---|
| 4,368,332 | 1/1983 | Jones et al. | 560/120 |
| 4,416,896 | 11/1983 | Nakane et al. | 546/256 |
| 4,430,345 | 2/1984 | Jones | 560/17 |
| 4,438,136 | 3/1984 | Jones et al. | 424/309 |
| 4,456,617 | 6/1984 | Nakane et al. | 546/256 |
| 4,458,091 | 7/1984 | Jones et al. | 562/502 |
| 4,596,823 | 6/1986 | Jones et al. | 548/222 |

OTHER PUBLICATIONS

Hiemstra et al., Tetrahedron Letters, No. 25, pp. 2183–2187 (1977).
Lemiere et al., J. Am. Chem. Soc. vol. 109, No. 5, pp. 1363–1370 (1987).
Piattner et al., J. Am. Chem. Soc., vol. 93, No. 7, pp. 1758–1761 (1970).
McMurry et al., Tetrahedron Letters, vol. 24, No. 10, pp. 979–982 (1983).
McMurry et al., Tetrahedron Letters, vol. 21, pp. 4313–4316 (1980).
Armstrong et al., "Competitive Antagonism at Thromboxane Receptors . . . ", Br. J. Pharmac. (1985) 84, 595–607.
Wilson et al., "Prostaglandin Endoperoxide . . . ", Advances in Pros., Throm. & Leukotriene Research vol. 14, 1985, pp. 393–425.
Nakane et al., "Aza-Substituted . . . ", Advances in Pros., Throm. & Leukotriene Research, 1985, vol. 15, 291.
Sprague et al., "Stereocontrolled Synthesis of . . . ", Advances in Pros., Throm. & Leukotriene Research, 1980, vol. 6, pp. 493–496.

*Primary Examiner*—Johann Richter
*Assistant Examiner*—J. Richter
*Attorney, Agent, or Firm*—Nixon & Vanderhye

[57] ABSTRACT

This invention relates to a process for preparing useful thromboxane $A_2$ inhibiting ($\pm$)7-[3α-[1-[[(phenylamino)thioxomethyl]hydrazono]ethyl]-1α,4α-bicyclo[2.2.1]hept-2β-yl]-heptenoic acids and useful derivatives thereof from ($\pm$)octahydro-1α-methyl-3aα,7aα-4α,7α-methano-2H-inden-2-ones.

27 Claims, No Drawings

PROCESS FOR PREPARING THROMBOXANE A₂ ANTAGONISTS

BACKGROUND OF THE INVENTION

Field of the Invention

This invention relates to a novel process that permits the unexpectedly efficient and convenient preparation of thromboxane $A_2$ inhibiting $(\pm)$7-[3α-[1-[[(phenylamino)-thioxomethyl]hydrazono]ethyl]-1α,α-bicyclo[2.2.1]hept-2β-yl]-heptenoic acids (hereinafter called "bicycloheptenoic acids") of Example 2 of U.S. Pat. No. 4,596,823, as well as its geometric isomer. The process is easily and conveniently adapted to the synthesis of a great number of derivatives of the subject bicycloheptenoic acids as disclosed in U.S. Pat. No. 4,596,823, having the general formula

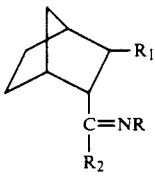

from compounds of the general formula

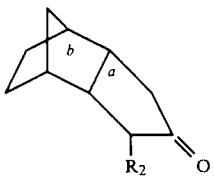

in which $R_1$ is a group of the formula $R'$—COQ where $R'$ is selected from the group consisting of —$(CH_2)_j$— where j is an integer from 4 to 8; and —$CH_2$—$CH=CH$—$(CH_2)_m$— where m is an integer from 1 to 5; and COQ is carboxy, a physiologically acceptable carboxylate salt (including such specific examples as alkali metals such as sodium, quaternary ammonium ions or amines such as tris, i.e. 2-amino-2-hydroxymethylpropane 1,3-diol), a $C_1$–$C_5$ alkyl ester or $CONHSO_2CH_3$; $R_2$ is selected from the group consisting of hydrogen, $C_{1-10}$ aliphatic hydrocarbon groups, and $C_{1-10}$ aliphatic hydrocarbon groups substituted by Ar, OAr or SAr, where Ar represents a phenyl, napthyl, fluorenyl, dibenzocyclohexyl, dibenzocycloheptyl, pyridyl, benzthiazolyl, dihydrobenzthiazolyl, N-methyldihydrobenzthiazolyl, benzoxazolyl, dihydrobenzoxazolyl or N-methyldihydrobenzoxazolyl group or such a group substituted by one or more substituents selected from $C_{1-10}$ alkoxy, halogen, $C_{1-10}$ halogen substituted alkyl, sulphamoyl, amino, hydroxyl, nitro and $C_{1-10}$ alkyl groups; and R is a group —$OR_3$, —$OR_4$, —A—$R_3$ or —$N=R_5$ in which A is —NH—, —NHCO— and —NHCONH—, —NH CO $CH_2N(R_6)$—, —NH $SO_2$—, or —NH CS NH— and wherein $R_3$ is a $C_{1-10}$ aliphatic hydrocarbon group, a group Ar or a $C_{1-10}$ aliphatic hydrocarbon group substituted by one or more groups selected from Ar, OAr and SAr; $R_4$ is substituted through an oxygen atom by a $C_{1-10}$ aliphatic hydrocarbon group which is itself substituted by one or more groups Ar; $R_5$ is a $C_{1-10}$ alphatic hydrocarbon group, a group Ar', where Ar' represents a fluorenylidene, dibenzocyclohexylidene, dibenzocycloheptylidene, dihydrobenzthiazolylidene, N-methyldihydrobenzthiazolylidene, dihydrobenzoxazolylidene or N-methyldihydrobenzoxazolylidene group or such a group substituted on a benzene ring or rings thereof by one or more substitutents selected from $C_{1-10}$ alkoxy, halogen, $C_{1-10}$ halogen-substituted alkyl, sulphamoyl, amino, hydroxyl, nitro and $C_{1-10}$ alkyl groups, or a $C_{1-10}$ aliphatic hydrocarbon group substituted by one or more groups selected from Ar, OAr and SAr; and $R_6$ is hydrogen, a $C_{1-10}$ aliphatic hydrocarbon group, a group Ar or a $C_{1-10}$ aliphatic hydrocarbon group substituted by one or more groups selected from Ar, OAr and SAr. These derivatives are more fully described in U.S. Pat. No. 4,596,823, the disclosure of which is incorporated herein by reference.

More specifically, this invention relates to a process for preparing bicycloheptenoic acids of Formula I in improved overall yield and purity by reacting a cyclic hemiacetal with a phosphonium ylide derived from an omeqa substituted fatty acid, oxidizing the resultant product to the corresponding ketone, and forming a hydrazone from the corresponding ketone.

This invention also relates to novel intermediates employed in the preparation of the thromboxane $A_2$ inhibiting bicycloheptenoic acid derivatives of Formula I.

SUMMARY OF THE INVENTION

This invention relates to a process for preparing compounds of general formula

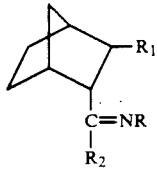

I wherein R, $R_1$ and $R_2$ are as previously described, which comprises the steps of:

(a) reacting a compound of the general formula

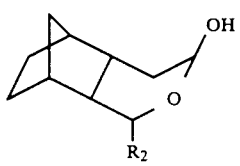

II wherein $R_2$ is as defined above, in the presence of a base with a compound of the general formula

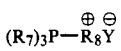

III wherein $R_8$ as defined above for $R_1$, with the proviso that $R_8$ has two fewer methylene groups than the species chosen for $R_1$, $R_7$ is aryl and Y is halogen, to yield a compound of the general formula

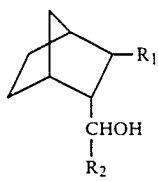

wherein $R_1$ and $R_2$ are as defined above;

(b) oxidizing the product of (a) to yield a compound of the general formula

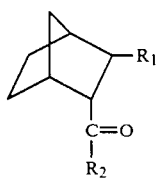

wherein $R_1$ and $R_2$ are as defined above; and (c) reacting the product of (b) with an amine of the formula

NH$_2$—R wherein R is as defined above. Additionally, prior to reacting the product of (b) with the above-described amine, the product of (b) can be inverted at the chiral center adjacent to the carbonyl group to yield its trans isomer.

More specifically, the process of the invention proceeds by (a) preparing a compound of the general formula:

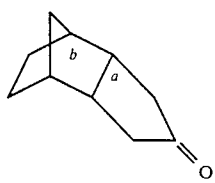

(b) modifying the compound of (a) to yield a compound of the formula

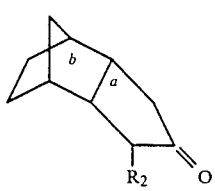

wherein $R_2$ is as defined above;

(c) oxidizing, by peracid oxidation, the ring 'a' of the product of (b) to yield a compound of the general formula

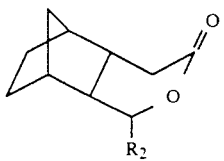

wherein $R_2$ is as defined above;

(d) reducing the product of (c) to yield a compound of the general formula

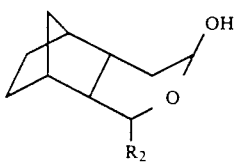

wherein $R_2$ is defined above;

(e) reacting the product of (d) in the presence of a base with a compound of the formula:

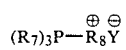

wherein $R_8$ is as defined above for $R_1$ with the proviso that $R_8$ has two fewer methylene groups than the species chosen for $R_1$, $R_7$ is aryl, and Y is halogen, to yield a compound of the general formula

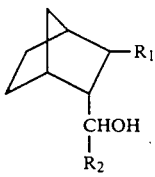

wherein $R_1$ and $R_2$ are as defined above;

(f) oxidation of the product of (e) to yield a compound of the general formula

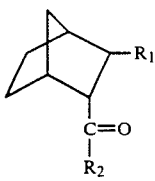

wherein $R_1$ and $R_2$ are as defined above; and (g) reacting the product of (f) with an amine of the general formula:

NH$_2$—R wherein R is as defined above.

Likewise, the product of (f) can be inverted at the chiral center adjacent to the carbonyl group to yield its trans isomer prior to hydrazone formation.

This invention also relates to intermediate compounds of the general formula

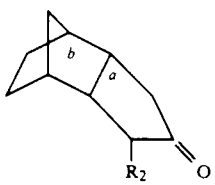

and the pharmaceutically acceptable salts thereof, wherein $R_2$ is as defined above.

This invention further relates to intermediate compounds of the general formula

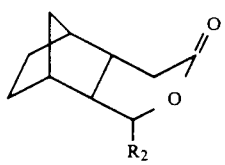

and the pharmaceutically acceptable salts thereof, wherein $R_2$ is as defined above.

This invention still further relates to intermediate compounds of the general formula

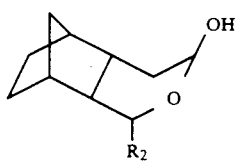

and the pharmaceutically acceptable salts thereof, wherein $R_2$ is as defined above.

This invention yet further relates to intermediate compounds of the general formula

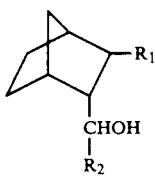

and the pharmaceutically acceptable salts thereof, wherein $R_1$ and $R_2$ are as defined above.

DETAILED DESCRIPTION OF THE INVENTION

Thromboxane $A_2(TXA_2)$, which is derived from arachidonic acid via prostaglandin $H_2(PGH_2)$, is implicated in several potentially noxious actions on various body systems, including platelet aggregation, bronchoconstriction and pulmonary and systemic vasoconstriction. Thus $TXA_2$ may be involved in the Normal sealing of blood vessels following injury, but in addition may contribute to pathological intravascular clotting or thrombosis. Furthermore, the constrictor actions of $TXA_2$ on bronchiolar, pulmonary vascular and systemic vascular smooth muscle may be important in the development of several anaphyllactic conditions including bronchial asthma. Furthermore, evidence exists that implicates $TXA_2$ as well as $PGH_2$ in the pathoqenesis of inflammation.

It is an object of the present invention to provide a route of synthesis resulting in greater convenience, efficiency and yield of compounds having activity at thromboxane $A_2$ receptor sites, and most especially of those compounds having such activity which are inhibitors of thromboxane $A_2$ activity and are therefore of interest in one or more areas of medical treatment including the treatment of thrombotic disorders, the treatment of anaphylactic disease states, and treatments utilizing anti inflammatory agents.

This invention prepares compounds, by the following general method of Scheme A, from ($\pm$)octahydro-1$\alpha$-methyl-3a$\alpha$, 7a$\alpha$-4$\alpha$,7$\alpha$-methano-2H-inden-2-one (formula III), or derivatives thereof, which can be prepared by methods well known to those skilled in the art.

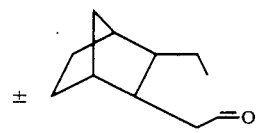

Scheme A

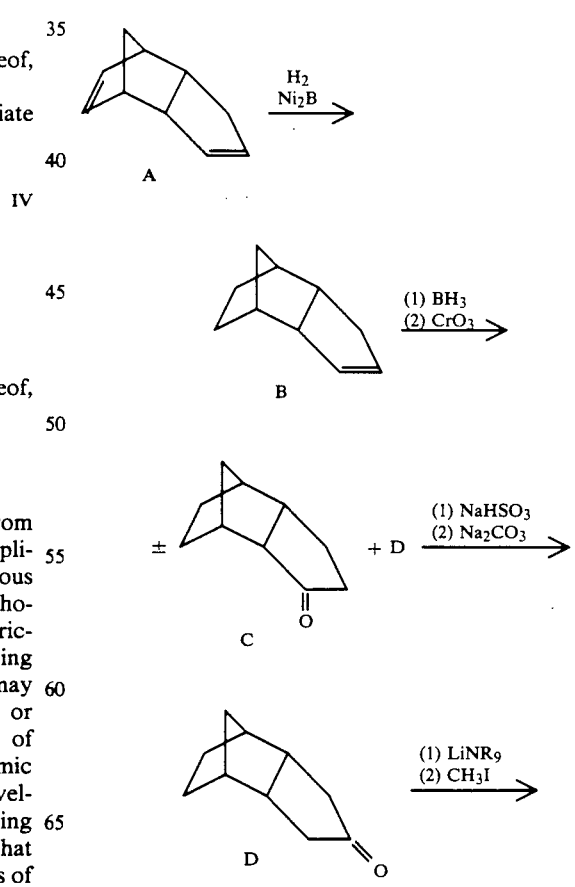

-continued
Scheme A
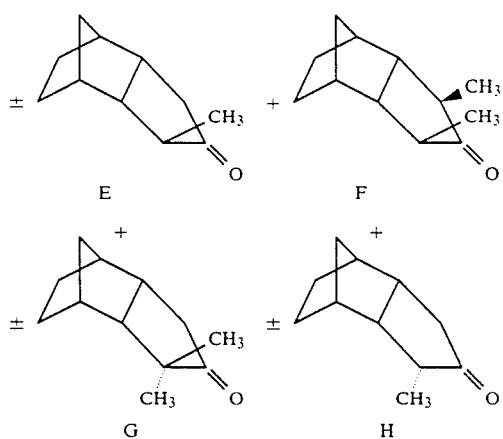
Following the preparation of compound E by such well-known methods, the synthesis of the desired compounds preferably proceeds, for example, as follows in Scheme B:
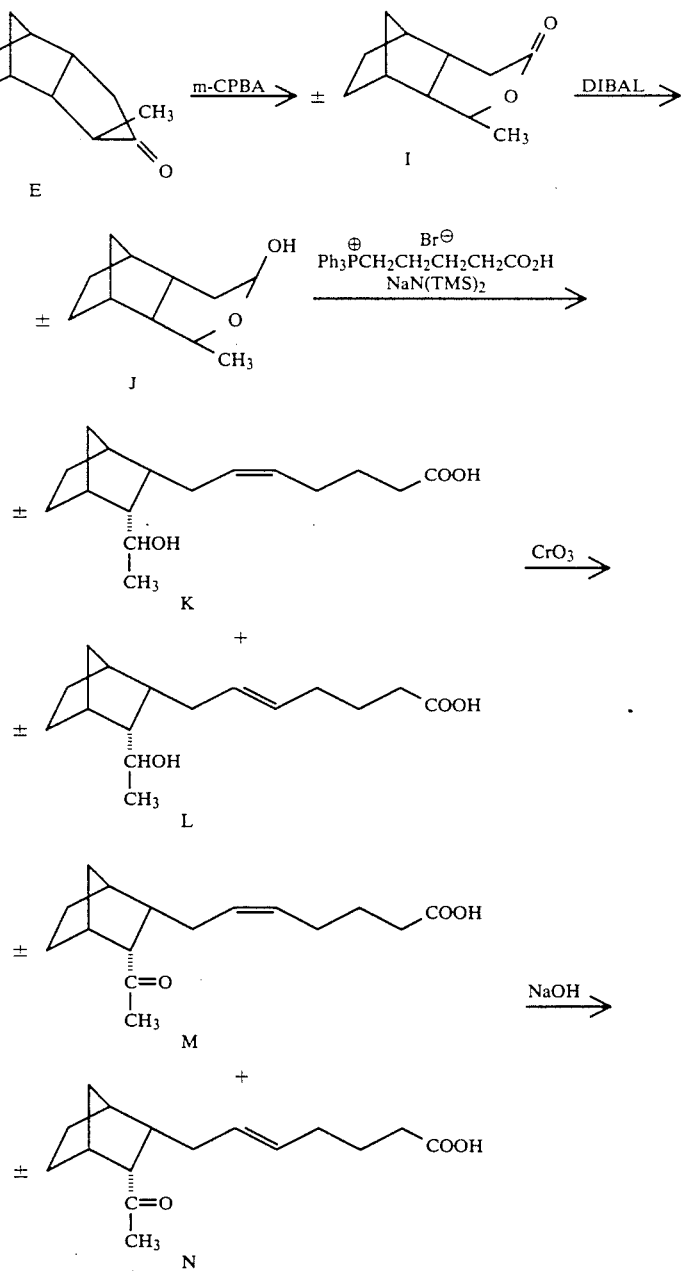

-continued

Scheme B

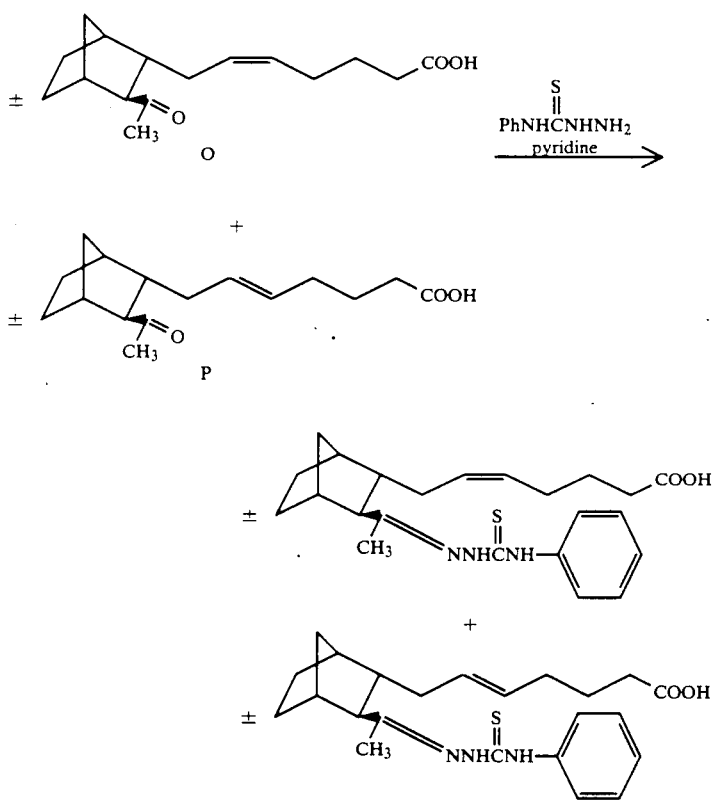

Where the group R' is of the form —(CH$_2$)$_j$—, it will be necessary to include a reduction step in order to convert the initially formed group R' having the formula —CH$_2$—CH=CH—(CH$_2$)$_m$—, where m is an integer equal to j—3, to the desired group —(CH$_2$)$_j$—. This is done by reduction either of the intermediate of formula IV or, more preferably, the intermediate of formula V, by reaction with hydrogen in the presence of a suitable catalyst, such as palladium on charcoal The preferred embodiments of this invention include intermediate compounds of the following general structure, used in the preparation of the corresponding thromboxane A$_2$ inhibiting bicycloheptenoic acid derivatives:

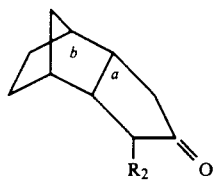

and the pharmaceutically acceptable salts thereof, wherein R$_2$ is as defined above.

More specifically, the preferred embodiments include compounds of the above formula wherein R$_2$ is C$_{1-10}$ aliphatic hydrocarbon, and most especially preferred is the above compound wherein R$_2$ is methyl, namely (±)octahydro-1α-methyl-3aα,7aα-4α,7α-methano-2H-inden-2-one,

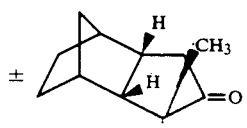

Secondarily illustrative of the preferred embodiments of this invention include compounds of the following general structure, likewise used in the preparation of corresponding thromboxane A$_2$ inhibiting bicycloheptenoic acid derivatives:

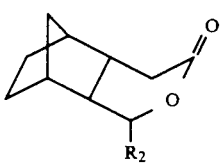

and the pharmaceutically acceptable salts thereof, wherein R$_2$ is as defined above.

More specifically, the preferred embodiments include compounds of the above formula wherein R$_2$ is C$_{1-10}$ aliphatic hydrocarbon, and most especially preferred is the above compound wherein R$_2$ is methyl, namely (±)octahydro-1α-methyl4aα,8aα,-5α,8α-methano-3H-2-benzopyran-3-one,

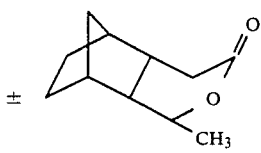

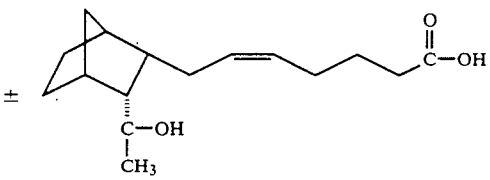

Thirdly illustrative of preferred embodiments of this invention include compounds of the following general structure, likewise used in the preparation of corresponding thromboxane $A_2$ inhibiting bicycloheptenoic acid derivatives

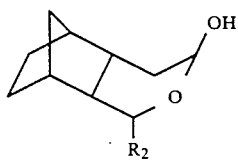

and the pharmaceutically acceptable salts thereof, wherein $R_2$ is as defined above.

More specifically, the preferred embodiments include compounds of the above formula wherein $R_2$ is $C_{1-10}$ aliphatic hydrocarbon, and most especially preferred is the above compound wherein R methyl, namely (±)octahydro-160 -methyl-4aα,8aα,-5α,8α-methano-1H-2-benzopyran-3-ol,

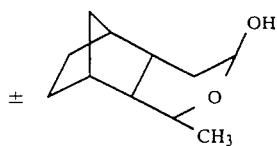

Fourthly illustrative of preferred embodiments of this invention include compounds of the following general structure, used in the preparation of corresponding thromboxane $A_2$ inhibiting bicycloheptenoic acid derivatives

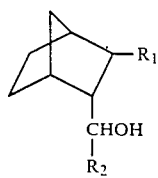

and the pharmaceutically acceptable salts thereof, wherein $R_1$ and $R_2$ are as defined above.

More specifically, the preferred embodiments include compounds of the above formula wherein $R_1$ is a group of the formula R'—COQ where R' is —(CH$_2$)$_j$— where j is an independent integer of from 5 to 7, especially 6, or particularly where R' is —CH$_2$—CH=CH—(CH$_2$)$_m$ where m is an independent integer of from 1 to 5, especially 2 to 4, and particularly 3; $R_2$ is $C_{1-10}$ aliphatic hydrocarbon, particularly methyl; and COQ is carboxy. Other preferred embodiments are the above compound wherein COQ is carboxy, m is 3 and $R_2$ is methyl, namely (±)7-[3β-(1R*-hydroxyethyl)-160 ,4α-bicyclo[2.2.1]hept-2α-yl]-5Z-heptenoic acid, The following examples further illustrate details for the method of preparation of the invention and for compounds of the invention. The invention, which is set forth in the foregoing disclosure, is not to be construed or limited in spirit or in scope by these examples. Those skilled in the art will readily understand that known variations of the conditions of the following preparative procedures can be used to prepare these compounds. All temperatures are degrees Celsius unless otherwise noted. In these reactions, it is also possible to make use of variations which are in themselves known, but are not mentioned here in greater detail. The compounds of the invention are readily prepared according to one of the following reaction schemes, or modifications thereof, using readily available starting materials, reagents and conventional synthesis procedures.

EXAMPLE 1

(±)3aα,4,7,7aα-tetrahydro 4α,7α-methano-1H-indene, A. Commercial dimer is suitable for use, if it has been protected from the air. A sample of a freshly opened Aldrich (Aldrich Chemical Company, 940 West St. Paul Ave., Milwaukee, Wis.) bottle showed only traces of impurities not present in a sample prepared by cracking the dimer and letting it dimerize over a period of weeks and then distilling under reduced pressure. The dimer is, however, susceptible to air oxidation. Old bottles have solids present and upon cracking provide quantities of water and leave a large pot residue

EXAMPLE 2

(±)3aα,4,5,6,7,7aα-hexahydro-4α,7α-methano-1H-indene, B. The hydrogenation over Nickel Boride, as described by Brown et al (Brown, H.C.; Rothberg. I.; VanderJagt, D.L., *J. Org. Chem* 1972, 37, 4098–4100) works quite well. Other catalysts tried gave extensive overreduction.

EXAMPLE 3

(±)octhydro-3aα,7aα-4α,7α-methano-2H-inden-2-one, D. The hydroboration should be carried out in the manner described by Brown, ibid. The bisulfite adduct is thick and hard to filter but it must be washed well with ether to remove all of the unsymmetrical ketone, (±)octahydro 3aα,7aα,-4α,7α-methano-1H-inden-1-one, C.

EXAMPLE 4

(±)octahydro 1α-methyl 3aα,7aα-4α,7α-methano-2H-inden-2 -one, E. To a solution of 6.9 mL (5.93 g, 41.9 mmole) of N-isopropylcyclohexylamine in 20 mL of dry THF cooled in a −78° bath was added 25 mL of 1.58 M n-butyllithium in hexane. After 15 min a solution of 5.62 g (37.5 mmole) of D in 20 mL of THF was added over 20 min. After 15 min more, 5 mL (11.4 q, 80 mmole) of methyl iodide was added quickly. (Alternatively, a methyl sulfonate can be used, such as methyl benzenesulfonate, methyl toluenesulfonate or methyl methanesulfonate.) After 30 min more, the mixture was allowed to warm to room temperature. After the addition of water (50 mL) the mixture was extracted twice with ether. After washing with water and brine and then drying over sodium sulfate, the solvents were evaporated and the residue was chromatographed (Flash, hexane EtOAc 99:1) to provide first 596 mg (9%) of (±)octahydro-1α, 3α-dimethyl-3aα, 7aα-4α,-7α-methano-2H-inden-2-one, F, followed by 3.81 g (62%) of E, and then a small amount of crude D. In some runs the early part of the E fraction contained (±)octahydro 1,1-dimethyl-3aα,7aα-4α,7α-methano-2H-inden-2-one. G. In a run which was allowed to stand at room temperature overnight before workup, a small amount of the isomeric (±)octahydro-1α-methyl-3aαβ,7αβ-4β,7β-methano-2-H-inden-2-one, H, followed the main product closely. This isomer also forms under acidic equilibration.

EXAMPLE 5

(±)octahydro- 1α-methyl-4aα,8aα,-5α,8α-methano-3-H-2-benzopyran-3-one, I. To a solution of 3.81 g (23.2 mmole) of E in 50 mL of dry methylene chloride was added 5.5 g (4.67 g, 27 mmole) of 85% m-chloroperoxybenzoic acid. After three days the solids were removed by filtration and rinsed with hexane. The filtrate was washed with sodium bicarbonate, water and brine. After evaporation of solvents chromatography (Flash, hexane EtOAc 98:2) provided 47 mq E with aryl-containing byproduct. This was followed by 4.02 q (96%) of I. Crystallization from a small amount of hexane provides solid melting at 51°-52.5°.

EXAMPLE 6

(±)octahydro-1α-methyl-4aα8aα,-5α,8α-methano-1H-2-benzopyran-3-ol, J. A solution of 4.02 g (22.3 mmole) of I in 5 mL of toluene was chilled in a −78° bath and 30 mL of 1 M DIBAL in toluene was added and stirred at −78° for 2 h. The mixture was quenched cautiously with 5 mL of MeOH. After warming to room temperature, 50 mL more MeOH was added. The solid was removed by filtration, rinsing thoroughly with MeOH. The filtrate was evaporated, and the residue was crystallized
from hexane to provide 3.23 q of J, mp 93°-94°. Chromatoqraphy of the mother liquors (Flash, 20–50 % EtOAc hexane) provided a small amount of crude I followed by a product fraction which was crystallized from hexane to provide an additional 0.33 g of J. Total yield: 3.56 g (88%).

EXAMPLE 7

(±)7-[3β-(1R*-hydroxyethyl)-1α,4α-bicyclo[2.2.1-]hept-2β-yl-5Z-heptenoic acid, K. To a suspension of 13.5 g (30.6 mmole) freshly crushed and dried (60°, high vac) (4-carboxybutyl)triphenylphosphonium bromide in 75 mL dry THF was added 60 mL of a 1 M sodium (bistrimethylsilyl)amide in THF. The mixture was stirred at room temperature for 18 h under nitrogen and then a solution of 3.38 g (18.5 mmole) of J in 50 mL of THF was added over 10 min. The temperature rose from 27° to 35° during the addition. During 1 h the color faded quickly and more white solids formed. After the addition of 100 mL of water the mixture was extracted with ether. The aqueous layer was acidified with 10 % HCl and extracted twice with ether washing with water and brine. After being dried over sodium sulfate the solvents were evaporated and the residue was chromatographed on a short acidic silica (such as BIOCILA by Bio-Rad ) column with 20% EtOAc-hexane to provide 4.90 g (99%) of a crude product fraction consisting of about 90% K and 10% of the 5E isomer, (±)7-3β-(1S-hydroxyethyl)-1α,4α-bicyclo[2.2.1]hept-2β-yl-5E-heptenoic acid, L. Traces of J could be recovered from the first ether extraction.

EXAMPLE 8

(±)7-(3β-acetyl-1α,4α-bicyclo[2.2.1]hept-2β-yl)-5Z-heptenoic acid, M and (±)7-(3α-acetyl-1α,4α-bicyclo[2.2.1]-hept-2β-yl)5Z-heptenoic acid, 0. A solution of 4.90 g (18 4 mmole) of crude K in 150 mL of acetone was chilled in an ice bath and titrated with Jones reagent (5.5 mL) until orange color persisted. The supernatant was decanted and concentrated to ca. 20 mL which was recombined with the solids and 100 mL of water. The mixture was extracted with ether. After washing with water and brine followed by drying over sodium sulfate the solvents were evaporated to leave 4.60 g of crude M with 10% of the 5E isomer (±)7(3β-acetyl-1α,4α-bicyclo[2.2.1]hept-2β-yl)-5E-heptenoic acid, N which had partially isomerized to 0 and its 5E isomer (±)7-(3α-acetyl-1α,4α-bicyclo[2.2.1]hept-2β-yl-5E-heptenoic acid, P. This material was dissolved in 50 mL of 1 N NaOH and stirred at room temperature for 1 h. After acidification with 10% HCl the product was extracted with ether which was washed with water and brine and dried over sodium sulfate. After evaporating solvents chromatography on a short acidic silica column (20% EtOAc hexane) provided 4.38 q (90%) of a mixture containing ca. 90% 0 and 10% P. No trace of M or N could be detected.

EXAMPLE 9

(±)7-[3α-[[(phenylamino)thioxomethyl]hydrazonoethyl]-1α, 4α-bicyclo[2.2.1]hept-2β-yl]-5Z-heptenoic acid, SC-44161. and (±)7-[3α-[[(phenylamino)thioxomethyl]hydrazonoethyl]-1α, 4α-bicyclo[2.2.1]hept-2β-yl]-5E-heptenoic acid, SC-46986 A solution of 1.20 g (4.5 mmole) of the mixture of O and P in 5 mL of pyridine was stirred at room temperature for 22 h. A solution of the mixture in 100 mL of methylene chloride was washed twice with 100 ML 5% HCl, water and brine. After drying over sodium sulfate and evaporation of solvent the residue was crystallized from 10 mL of ether to provide 1.364 g (73%) of product, mp 129°-132°.

While the invention has been described and illustrated with reference to certain prepared embodiments and certain illustrative steps, those skilled in the art will appreciate that various changes, modifications and substitutions can be made therein without departing from the spirit and scope of the invention. It is intended therefore that the invention be limited only by the scope of the claims which follow, and that such claims be interpreted as broadly as is reasonable.

What is claimed is:
1. A method for producing compounds of the formula

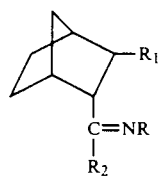

I wherein
$R_1$ is a group of the formula R'—COQ where R' is —$(CH_2)_j$— where j is an integer from 4 to 8 and COQ is carboxy, a physiologically acceptable carboxylate salt, a $C_1$–$C_5$ alkyl ester or CONHSO$_2$CH$_3$;

$R_2$ is selected from the group consisting of hydrogen, $C_{1-10}$ aliphatic hydrocarbon groups, and $C_{1-10}$ aliphatic hydrocarbon groups substituted by Ar, OAr or SAr, where Ar represents a phenyl, naphthyl, fluorenyl, dibenzocyclohexyl, dibenzocycloheptyl, pyridyl, benzthiazolyl, dihydrobenzthiazolyl, N-methyldihydrobenzthiazolyl, benzoxazolyl, dihydrobenzoxazolyl or N-methyldihydrobenzoxazolyl group or such a group substituted by one or more substituents selected from $C_{1-10}$ alkoxy, halogen, $C_{1-10}$ halogen-substituted alkyl, sulphamoyl, amino, hydroxyl, nitro and $C_{1-10}$ alkyl groups;

and R is a group —OR$_3$, —A—R$_3$ or —N=R$_5$ in which A is —NH—, —NHCO—, —NHCONH—, —NHCOCH$_2$N(R$_6$)—, —NHSO$_2$—, or —NHCSNH— and wherein R$_3$ is a $C_{1-10}$ aliphatic hydrocarbon group, a group Ar or a $C_{1-10}$ aliphatic hydrocarbon group substituted by one or more groups selected from Ar, OAr and SAr; R$_5$ is a $C_{1-10}$ aliphatic hydrocarbon group, a group Ar', where Ar' represents a fluorenylidene, dibenzocyclohexylidene, dibenzocycloheptylidene, dihydrobenzthiazolylidene, N-methyldihydrobenzthiazolylidene, dihydrobenzoxazolylidene or N-methyldihydrobenzoxazolylidene group or such a group substituted on a benzene ring or rings thereof by one or more substituents selected from $C_{1-10}$ alkoxyl, halogen, $C_{1-10}$ halogen-substituted alkyl, sulphamoyl, amino, hydroxyl, nitro and $C_{1-10}$ alkyl groups, or a $C_{1-10}$ aliphatic hydrocarbon group substituted by one or more groups selected from Ar, OAr and SAr; and R$_6$ is hydrogen, a $C_1$-aliphatic hydrocarbon group, a group Ar or a $C_{1-10}$ aliphatic hydrocarbon group substituted by one or more groups selected from Ar, OAr and SAr, which method comprises the steps of:

(a) reacting a compound of the formula

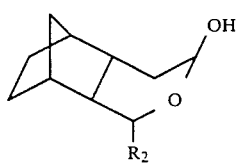

II wherein R$_2$ is a defined above, in the presence of a base with a compound of the formula

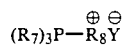

III wherein R$_8$ is a saturated straight chain alkylene group with a chain length of two carbon atoms less than that of R$_1$, R$_7$ is aryl and Y is halogen, to yield a compound of the formula

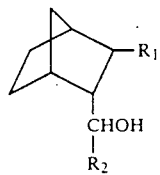

IV wherein R$_1$ is a group of the formula R'COQ in which R' is —CH$_2$—CH=CH—(CH$_2$)$_m$— where m is an integer from 1 to 5; and COQ and R$_2$ are as defined above; the group R' in the compound of formula IV then being reduced to the group —(CH$_2$)$_j$— present in the compound of formula I;

(b) oxidizing the product of (a) to yield a compound of the formula

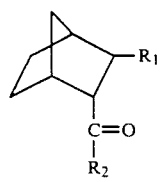

V wherein R$_1$ and R$_2$ are as defined above for the compound of formula I; and (c) reacting the product of (b) with an amine of the formula

NH$_2$—R wherein R is as defined above.

2. A method for producing compounds of the formula

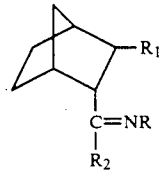

I wherein
R$_1$ is a group of the formula R'—COQ where R' is —(CH$_2$)$_j$— where j is an integer from 4 to 8 and COQ is carboxy, a physiologically acceptable carboxylate salt, a $C_1$–$C_5$ alkyl ester or CONHSO$_2$CH$_3$;

R$_2$ is selected from the group consisting of hydrogen, $C_{1-10}$ aliphatic hydrocarbon groups, and $C_{1-10}$ aliphatic hydrocarbon groups substituted by Ar, OAr or SAr, where Ar represents a phenyl, naphthyl, fluorenyl, dibenzocyclohexyl, dibenzocycloheptyl, pyridyl, benzthiazolyl, dihydrobenzthiazolyl, N-methyldihydrobenzthiazolyl, benzoxazolyl, dihydrobenzoxazolyl or N-methyldihydrobenzoxazolyl group or such a group substituted by one or more substituents selected from $C_{1-10}$ alkoxy, halogen, $C_{1-10}$ halogen-substituted alkyl, sulphamoyl, amino, hydroxyl, nitro and $C_{1-10}$ alkyl groups;

and R is a group —OR$_3$, —A—R$_3$ or —N=R$_5$ in which A is —NH—, —NHCO—, —NHCONH—, —NHCOCH$_2$N(R$_6$)—, —NHSO$_2$—, or —NHCSNH— and wherein R$_3$ is a $C_1$ aliphatic hydrocarbon group, a group Ar or a $C_{1-10}$ aliphatic hydrocarbon group substituted by one or more groups selected from AR, OAr and SAr; $R_5$ is a $C_{1-10}$ aliphatic hydrocarbon group, a group Ar', where Ar' represents a fluorenylidene, dibenzocyclohexylidene, dibenzocycloheptylidene, dihydrobenzthiazolylidene, N-methyldihydrobenzthiazolylidene, dihydrobenzoxazolylidene or N-methyldihydrobenzoxazolylidene group or such a group substituted on a benzene ring or rings thereof by one or more substituents selected from $C_{1-10}$ alkoxy, halogen, $C_{1-10}$ halogen-substituted alkyl, sulphamoyl, amino, hydroxyl, nitro and $C_{1-10}$ alkyl groups, or a $C_{1-10}$ aliphatic hydrocarbon group substituted by one or more groups selected from Ar, OAr and SAr; and $R_6$ is hydrogen, a $C_{1-10}$ aliphatic hydrocarbon group, a group Ar or a $C_{1-10}$ aliphatic hydrocarbon group substituted by one or more groups selected from Ar, OAr and SAr, which method comprises the steps of:

(a) reacting a compound of the formula

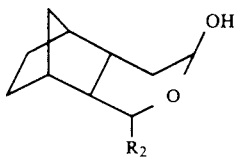

II wherein $R_2$ is a defined above, in the presence of a base with a compound of the formula

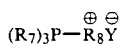

III wherein $R_8$ is a saturated straight chain alkylene group with a chain length of two carbon atoms less than that of $R_1$, $R_7$ is aryl and Y is halogen, to yield a compound of the formula

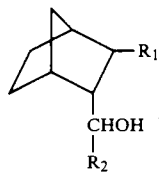

IV wherein $R_1$ is a group of the formula R'COQ in which R' is —CH$_2$—CH=CH—(CH$_2$)$_m$— where m is an integer from 1 to 5; and COQ and $R_2$ are as defined above;

(b) oxidizing the product of (a) to yield a compound of the formula

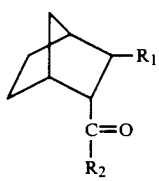

V

=wherein $R_1$ is —CH$_2$—CH=CH—(CH$_2$)$_m$— where m is an integer from 1 to 5; and COQ and $R_2$ are as defined above, the group R' in the compound of the formula V then being reduced to the group —(CH$_2$)$_j$— present in the compound of formula I; and (c) reacting the product of (b) with an amine of the formula $$NH_2—R$$

where R is as defined above.

3. A method for producing compounds of the formula

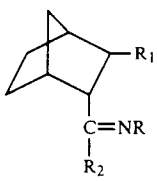

I wherein $R_1$ is a group of the formula R'—COQ where R' is —CH$_2$—CH=CH—(CH$_2$)$_m$— where m is an integer from 1 to 5 and COQ is carboxy, a physiologically acceptable carboxylate salt, a $C_1$-$C_5$ alkyl ester or CONHSO$_2$CH$_3$;

$R_2$ is selected from the group consisting of hydrogen, $C_{1-10}$ aliphatic hydrocarbon groups, and $C_{1-10}$ aliphatic hydrocarbon groups substituted by Ar, OAr or SAr, where Ar represents a phenyl, naphthyl, fluorenyl, dibenzocyclohexyl, dibenzocycloheptyl, pyridyl, benzthiazolyl, dihydrobenzthiazolyl, N-methyldihydrobenzthiazolyl, benzoxazolyl, dihydrobenzoxazolyl or N-methldihydrobenzoxazolyl group or such a group substituted by one or more substituents selected from $C_1$ alkoxy, halogen, $C_{1-10}$ halogen-substituted alkyl, sulphamoyl, amino, hydroxyl, nitro and $C_1$ alkyl groups;

and R is a group —OR$_3$, —A—R$_3$ or —N=R$_5$ in which A is —NH—, —NHCO—, —NHCONH—, —NHCOCH$_2$N(R$_6$)—, —NHSO$_2$—, or —NHCSNH— and wherein R$_3$ is a $C_{1-10}$ aliphatic hydrocarbon group, a group Ar or a $C_{1-10}$ aliphatic hydrocarbon group substituted by one or more groups selected from AR, OAr and SAr; $R_5$ is a $C_{1-10}$ aliphatic hydrocarbon group, a group Ar'. where Ar' represents a fluorenylidene, dibenzocyclohexylidene, dibernzocycloheptylidene, dihydrobenzthiazolylidene, N-methyldihydrobenzthiazolylidene, dihydrobenzoxazolylidene or N-methyldihydrobenzoxazolylidene group or such a group substituted on a benzene ring or rings thereof by one or more substitutents selected from $C_{1-10}$ alkoxy, halogen, $C_{1-10}$ halogen-substituted alkyl, sulphamoyl, amino, hydroxyl, nitro and $C_{1-10}$ alkyl groups, or a $C_{1-10}$ aliphatic hydrocarbon group substituted by one or more groups selected from Ar, OAr and SAr; and $R_6$ is hydrogen, a $C_{1-10}$ aliphatic hydrocarbon group, a group AR or a $C_{1-10}$ aliphatic hydrocarbon group substituted by one or more groups selected from Ar, OAr and SAr, which method comprises the steps of:

(a) reacting a compound of the general formula

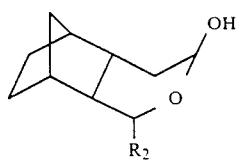
II wherein $R_2$ is a defined above, in the presence of a base with a compound of the formula

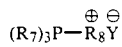
III wherein $R_8$ is a saturated straight chain alkylene group with a chain length of two carbon atoms less than that of $R_1$, $R_7$ is aryl and Y is halogen, to yield a compound of the formula

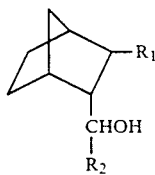
IV wherein $R_1$ and $R_2$ are as defined above;

(b) oxidizing the product of (a) to yield a compound of the formula

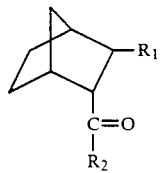
V wherein $R_1$ and $R_2$ are as defined above; and (c) reacting the product of (b) with an amine of the formula $$NH_2-R$$

wherein R is as defined above.

4. The method as claimed in claim 1, 2 or 3 which includes the additional step of inversion of the compound of formula V.

5. The method as claimed in claim 1, 2 or 3, in which the amine used is the compound

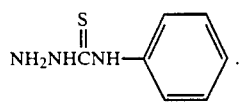

6. A method for producing compounds of the formula

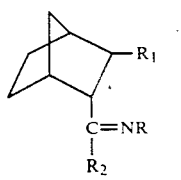
I wherein $R_1$ is a group of the formula $R'-COQ$ where $R'$ is $-(CH_2)_j-$ where j is an integer from 4 to 8; and COQ is carboxy, a physiologically acceptable carboxylate salt, a $C_{1-10}$ alkyl ester or $CONHSO_2CH_3$;

$R_2$ is selected from the group consisting of hydrogen, $C_{1-10}$ aliphatic hydrocarbon groups, and $C_{1-10}$ aliphatic hydrocarbon groups substituted by Ar, OAr or SAr, where Ar represents a phenyl, naphthyl, fluorenyl, dibenzocyclohexyl, dibenzocycloheptyl, pyridyl, benzthiazolyl, dihydrobenzthiazolyl, N-methyldihydrobenzthiazolyl, benzoxazolyl, dihydrobenzoxazolyl or N-methyldihydrobenzoxazolyl group or such a group substituted by one or more substituents selected from $C_{1-10}$ alkoxy, halogen, $C_{1-10}$ halogen-substituted alkyl, sulphamoyl, amino, hydroxyl, nitro and $C_{1-10}$ alkyl groups;

and R is a group $-OR_3$, $-A-R_3$ or $-N=R_5$ in which A is $-NH-$, $-NHCO-$, $-NHCONH-$, $-NHCOCH_2N(R_6)-$, $-NHSO_2-$, or $-NHCSNH-$ and wherein $R_3$ is a $C_{1-10}$ aliphatic hydrocarbon group, a group Ar or a $C_{1-10}$ aliphatic hydrocarbon group substituted by one or more groups selected from Ar, OAr and SAr; $R_5$ is a $C_{1-10}$ aliphatic hydrocarbon group, a group Ar', where Ar' represents a fluorenylidene, dibenzocyclohexylidene, dibenzocycloheptylidene, dihydrobenzthiazolylidene, N-methyldihydrobenzthiazolylidene, dihydrobenzoxazolylidene or N-methyldihydrobenzoxazolylidene group or such a group substituted on a benzene ring or rings thereof by one or more substitutents selected from $C_{1-10}$ alkoxy, halogen, $C_{1-10}$ halogen-substituted alkyl, sulphamoyl, amino, hydroxyl, nitro and $C_{1-10}$ alkyl groups, or a $C_{1-10}$ aliphatic hydrocarbon group substituted by one or more groups selected from Ar, OAr and SAr; and $R_6$ is hydrogen, a $C_{1-10}$ aliphatic hydrocarbon group, a group AR or a $C_{1-10}$ aliphatic hydrocarbon groups substituted by one or more groups selected from Ar, OAr and SAr, which method comprises the steps of:

(a) preparing a compound of the formula:

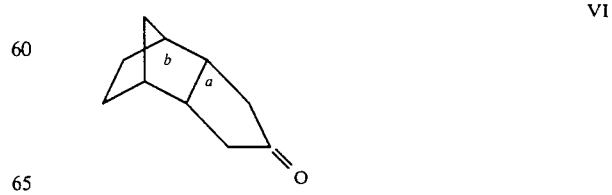
VI (b) modifying the compound of formula VI to yield a compound of the formula

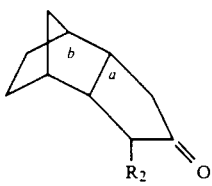

wherein $R_2$ is as defined above;

(c) oxidizing, by peracid oxidation, the ring 'a' of the compound of formula VII to yield a compound of the formula

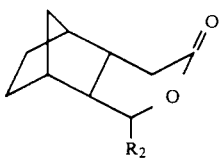

wherein $R_2$ is as defined above;

(d) reducing the product of (c) to yield a compound of the formula

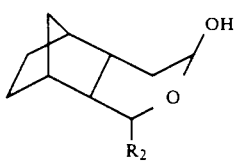

wherein $R_2$ is as defined above;

(e) reacting the product of (d) in the presence of a base with a compound of the formula:

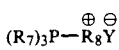

wherein $R_8$ is a saturated straight chain alkylene group with a chain length of two carbon atoms less than that of $R_1$, $R_7$ is aryl, and Y is halogen, to yield a compound of the formula wherein $R_1$ is a group of the formula R'COQ; in which R' is —CH$_2$—CH=CH—(CH$_2$)$_m$— where m is an integer from 1 to 5; and COQ and $R_2$ are as defined above, the group R' in the compound of formula IV then being reduced to the group —(CH$_2$)$_j$— present in the compound of formula I;

(f) oxidizing the product of (e) to yield a compound of the formula

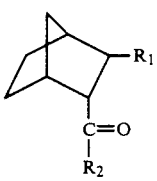

wherein $R_1$ and $R_2$ are as defined above for the compound of formula (I); and (g) reacting the product of (f) with an amine of the formula

NH$_2$—R wherein R is as defined above.

7. A method for producing compounds of the formula

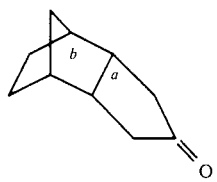

wherein $R_1$ is a group of the formula R'—COQ in which R' is —(CH$_2$)$_j$— where j is an integer from 4 to 8; and COQ is carboxy, a physiologically acceptable carboxylate salt, a C$_{1-10}$ alkyl ester or CONHSO$_2$CH$_3$;

$R_2$ is selected from the group consisting of hydrogen, C$_{1-10}$ aliphatic hydrocarbon groups, and C$_{1-10}$ aliphatic hydrocarbon groups substituted by Ar, OAr or SAr, where Ar represents a phenyl, naphthyl, fluorenyl, dibenzocyclohexyl, dibenzocycloheptyl, pyridyl, benzthiazolyl, dihydrobenzthiazolyl, N-methyldihydrobenzthiazolyl, benzoxazolyl, dihydrobenzoxazolyl or N-methyldihydrobenzoxazolyl group or such a group substituted by one or more substituents selected from C$_{1-10}$ alkoxy, halogen, C$_{1-10}$ halogen-substituted alkyl, sulphamoyl, amino, hydroxyl, nitro and C$_{1-10}$ alkyl groups;

and R is a group —OR$_3$, —A—R$_3$ or —N=R$_5$ in which A is —NH—, —NHCO—, —NHCONH—, —NHCOCH$_2$N(R$_6$)—, —NHSO$_2$—, or —NHCSNH— and wherein R$_3$ is a C$_{1-10}$ aliphatic hydrocarbon group, a group Ar or a C$_{1-10}$ aliphatic hydrocarbon group substituted by one or more groups selected from Ar, OAr and SAr; R$_5$ is a C$_{1-10}$ aliphatic hydrocarbon group, a group Ar', where Ar' represents a fluorenylidene, dibenzocyclohexylidene, dibenzocycloheptylidene, dihydrobenzthiazolylidene, N-methyldihydrobenzthiazolylidene, dihydrobenzoxazolylidene or N-methyldihydrobenzoxazolylidene group or such a group substituted on a benzene ring or rings thereof by one or more substituents selected from C$_{1-10}$ alkoxy, halogen, C$_{1-10}$ halogen-substituted alkyl, sulphamoyl, amino, hydroxyl, nitro and C$_{1-10}$ alkyl groups, or a C$_{1-10}$ aliphatic hydrocarbon group substituted by one or more groups selected from Ar, OAr and SAr; and R$_6$ is hydrogen, a C$_{1-10}$ aliphatic hydrocarbon group, a group Ar or a C$_{1-10}$ aliphatic hydrocarbon groups substituted by one or more groups selected from Ar, OAr and SAr, which method comprises the steps of:

(a) preparing a compound of the formula:

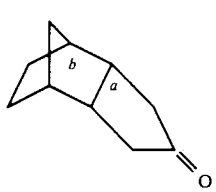

(b) modifying the compound of formula VI to yield a compound of the formula

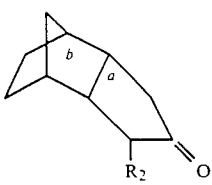

VII wherein R₂ is as defined above;

(c) oxidizing, by peracid oxidation, the ring 'a' of the compound of formula VII to yield a compound of the formula

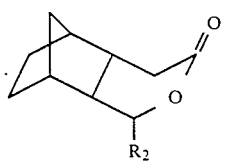

VIII wherein R₂ is as defined above;

(d) reducing the product of (c) to yield a compound of the formula

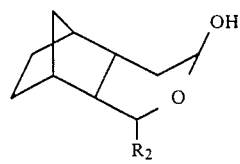

II wherein R₂ is as defined above;

(e) reacting the product of (d) in the presence of a base with a compound of the formula:

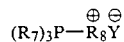

III wherein $R_8$ is a saturated straight chain alkylene group with a chain length of two carbon atoms less than that of $R_1$, $R_7$ is aryl, and Y is halogen, to yield a compound of the formula

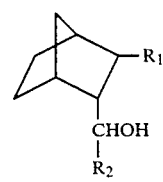

IV wherein $R_1$ is a group of the formula R'COQ; where R' is $-CH_2-CH=CH-(CH_2)_m-$ where m is an integer from 1 to 5; and COQ and $R_2$ are as defined above;

(f) oxidizing the product of (e) to yield a compound of the formula

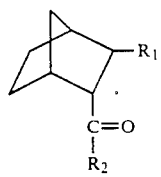

V wherein $R_1$ is $-CH_2-CH=CH-(CH_2)_m-$ where m is an integer of 1 to 5 and COQ and and $R_2$ are as defined above; the group R' in the compound of formula V then being reduced to the group $-(CH_2)_j-$ present in the compound of formula I; and (g) reacting the product of (f) with an amine of the formula

NH₂—R wherein R is as defined above.

8. A method for producing compounds of the formula

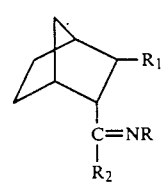

I wherein $R_1$ is a group of the formula R'—COQ where R' is $-CH_2-CH=CH-(CH_2)_m-$ where m is an integer from 1 to 5; and COQ is carboxy, a physiologically acceptable carboxylate salt, a $C_{1-10}$ alkyl ester or CONHSO₂CH₃;

$R_2$ is selected from the group consisting of hydrogen, $C_{1-10}$ aliphatic hydrocarbon groups, and $C_{1-10}$ aliphatic hydrocarbon groups substituted by Ar, OAr or SAr, where Ar represents a phenyl, naphthyl, fluorenyl, dibenzocyclohexyl, dibenzocycloheptyl, pyridyl, benzthiazolyl, dihydrobenzthiazolyl, N-methyldihydrobenzthiazolyl, benzoxazolyl, dihydrobenzoxazolyl or N-methyldihydrobenzoxazolyl group or such a group substituted by one or more substituents selected from $C_{1-10}$ alkoxy, halogen, $C_{1-10}$ halogen-substituted alkyl, sulphamoyl, amino, hydroxyl, nitro and $C_{1-10}$ alkyl groups;

and R is a group $-OR_3$, $-A-R_3$ or $-N=R_5$ in which A is $-NH-$, $-NHCO-$, $-NHCONH-$, $-NHCOCH_2N(R_6)-$, $-NHSO_2-$, or $-NHCSNH-$ and wherein $R_3$ is a $C_{1-10}$ aliphatic hydrocarbon group, a group Ar or a $C_{1-10}$ aliphatic hydrocarbon group substituted by one or more groups selected from Ar, OAr and SAr; $R_5$ is a $C_{1-10}$ aliphatic hydrocarbon group, a group Ar', where Ar' represents a fluorenylidene, dibenzocyclohexylidene, dibenzocycloheptylidene, dihydrobenzthiazolylidene, N-methyldihydrobenzthiazolylidene, dihydrobenzoxazolylidene or N-methyldihydrobenzoxazolylidene group or such a group substituted on a benzene ring or rings thereof by one or more substituents selected from $C_{1-10}$ alkoxy, halogen, $C_{1-10}$ halogen-substituted alkyl, sulphamoyl, amino, hydroxyl, nitro and $C_{1-10}$ alkyl groups, or a $C_{1-10}$ aliphatic hydrocarbon group substituted by one or more groups selected from Ar, OAr and SAr; and $R_6$ is hydrogen, a $C_{1-10}$ aliphatic hydrocarbon group, a group Ar or a $C_{1-10}$ aliphatic hydrocarbon groups substituted by one or more groups selected from Ar, OAr and SAr, which method comprises the steps of:

(a) preparing a compound of the formula:

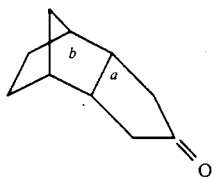
VI (b) modifying the compound of formula VI to yield a compound of the formula

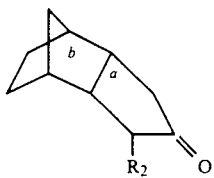
VII wherein $R_2$ is as defined above;

(c) oxidizing, by peracid oxidation, the ring 'a' of the compound of formula VII to yield a compound of the formula

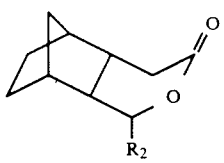
VIII wherein $R_2$ is as defined above;

(d) reducing the product of (c) to yield a compound of the formula

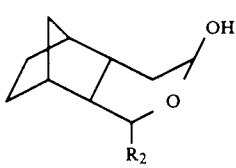
II wherein $R_2$ is as defined above;

(e) reacting the product of (d) in the presence of a base with a compound of the formula:

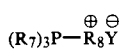
III wherein $R_8$ is a saturated straight chain alkylene group with a chain length of two carbon atoms less than that of $R_1$, $R_7$ is aryl, and Y is halogen, to yield a compound of the formula

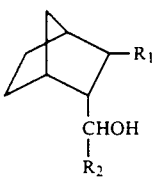
IV wherein $R_1$ and $R_2$ are as defined above;

(f) oxidizing the product of (e) to yield a compound of the formula

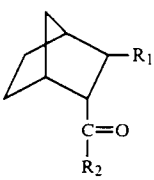
V wherein $R_1$ and $R_2$ are as defined above; and (g) reacting the product of (f) with an amine of the formula $$NH_2-R$$

wherein R is as defined above.

9. The process as claimed in claim 6, 7 or 8, which includes the additional step of inversion of the compound of formula V.

10. A method for producing compounds of the formula

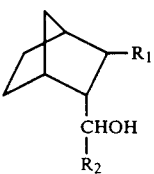
IV wherein
$R_1$ is a group of the formula R'—COQ where R' is —$CH_2$—CH=CH—$(CH_2)_m$— where m is an integer of 1 to 5; and COQ is carboxy, a physiologically acceptable carboxylate salt, a $C_{1-5}$ alkyl ester or $CONHSO_2CH_3$; and $R_2$ is selected from the group consisting of hydrogen, a $C_{1-10}$ aliphatic hydrocarbon groups, and $C_{1-10}$ aliphatic hydrocarbon groups substituted by AR, OAr or SAr, where Ar represents a phenyl, naphthyl, fluorenyl, dibenzocyclohexyl, dibenzocycloheptyl, pyridyl, benzthiazolyl, dihydrobenzthiazolyl, N-methyldihydrobenzthiazolyl, benzoxazolyl, dihydrobenzoxazolyl, or N-methyldihydrobenzoxazolyl group or such a group substituted by one or more substitutents selected from $C_{1-10}$ alkoxy, halogen, $C_{1-10}$ halogen-substituted alkyl, sulphamoyl, amino, hydroxyl, nitro and $C_{1-10}$ alkyl groups; which method comprises the steps of:

(a) preparing a compound of the formula

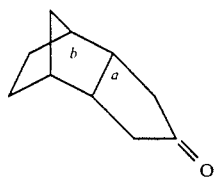
VI (b) reacting the compound of formula VI with a compound of the formula

R₂X wherein R₂ is as defined above and X is a halogen, such reaction taking place in the presence of a strong base;

(c) oxidizing, by peracid oxidation, the product of (b) to yield a compound of the formula VIII;

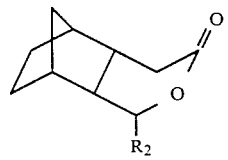
VIII (d) reducing the product of formula VIII to yield a compound of the formula

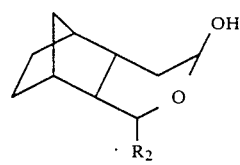
II wherein R₂ is as defined above;

(e) reacting the product of formula II with a compound of the formula $(R_7)_3 \overset{\oplus}{P} - \overset{\ominus}{R_8} Y$    III wherein R₈ is a saturated straight chain alkylene group with a chain length of two carbon atoms less than that of R₁, R₇ is aryl and Y is halogen, to yield a product of the formula

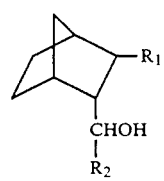
IV wherein R₁ and R₂ are as defined above.

11. A method for producing compounds of the formula

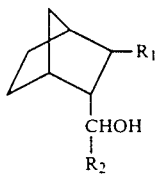
IV wherein $R_1$ is a group of the formula R'—COQ where R' is —(CH₂)ⱼ— where j is an integer from 4 to 8; and COQ is carboxy, a physiologically acceptable carboxylate salt, a C₁₋₅ alkyl ester or CONHSO₂CH₃; and R₂ is selected from the group consisting of hydrogen, a C₁₋₁₀ aliphatic hydrocarbon groups, and C₁₋₁₀ aliphatic hydrocarbon groups substituted by Ar, OAr or SAr, where Ar represents a phenyl, naphthyl, fluorenyl, dibenzocyclohexyl, dibenzocycloheptyl, pyridyl, benzthiazolyl, dihydrobenzthiazolyl, N-methyldihydrobenzthiazolyl, benzoxazolyl, dihydrobenzoxazolyl, or N-methyldihydrobenzoxazolyl group or such a group substituted by one or more substituents selected from C₁₋₁₀ alkoxy, halogen, C₁₋₁₀ halogen-substituted alkyl, sulphamoyl, amino, hydroxyl, nitro and C₁₋₁₀ alkyl groups; which method comprises the steps of preparing a compound of the formula IV as claimed in claim 10 by carrying out the steps (a) to (e) of claim 10 and then reducing the group R' in the compound of claim 10 to the group —(CH₂)ⱼ— present in the compound of formula IV as defined above.

12. A method as claimed in claim 10, in which the base used in step (b) is a compound of the formula LiNR₉ wherein R₉ is C₁₋₁₀ aliphatic hydrocarbon.

13. The method as claimed in claim 12, in which the base used is n-butyllithium.

14. The method as claimed in claim 10, in which the reagent of the formula R₂X used in step (b) is CH₃I.

15. The method as claimed in claim 10, in which the peracid oxidation of step (c) is performed in the presence of an oxidizing agent selected from the group consisting of peroxymonosulfuric acid, peroxybenzoic acid, monoperoxyphthalic acid, peroxyacetic acid, trifluoroperoxyacetic acid and chloroperoxybenzoic acid.

16. The method as claimed in claim 15, in which the oxidizing agent is selected from the group consisting of o-chloroperoxybenzoic acid, m-chloroperoxybenzoic acid and p-chloroperoxybenzoic acid.

17. The method as claimed in claim 16, in which the oxidizing agent is m-chloroperoxbenzoic acid.

18. The method as claimed in claim 10, in which the reducing agent employed in step (d) is diisobutylaluminum hydride.

19. The method as claimed in claim 10, in which R₇ in the compound of formula III employed in step (e) is phenyl.

20. The method as claimed in claim 10, in which Y in the reactant of formula III used in step (e) is bromine.

21. The method as claimed in claim 10, in which the reactant of formula III used in step (e) is (4-carboxybutyltriphenylphosphonium bromide.

22. A method of producing compounds of the formula

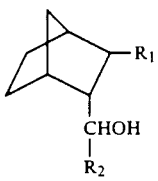

IV wherein R₁ is a group of the formula R'-COQ where R' is —CH₂—CH=CH—(CH₂)$_m$— where m is an integer from 1 to 5; and COQ is carboxy, a physiologically acceptable carboxylate salt, a $C_1$-$C_5$ alkyl ester or CONHSO₂CH₃; and R₂ is selected from the group consisting of hydrogen, $C_{1-10}$ aliphatic hydrocarbon groups, and $C_{1-10}$ aliphatic hydrocarbon groups substituted by Ar, OAr and SAr, where Ar represents a phenyl, naphthyl, fluorenyl, dibenzocyclohexyl, dibenzocycloheptyl, pyridyl, benzthiazolyl, dihydrobenzthiazolyl, N-methyldihydrobenzthiazolyl, benzoxazolyl, dihydrobenzoxazolyl or N-methyldihydrobenzoxazolyl group or such a group substituted by one or more substituents selected from $C_{1-10}$ alkoxy, halogen, $C_{1-10}$ halogen-substituted alkyl, sulphamoyl, amino, hydroxyl, nitro and $C_{1-10}$ alkyl groups; which methods comprises the steps of:

(a) reducing a compound of the formula

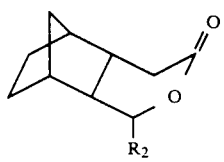

VIII wherein R₂ is as defined above to provide a compound of the formula

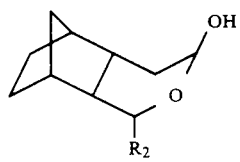

II wherein R₂ is as defined above; and (b) reacting the compound of formula II in the presence of a base with a compound of the formula

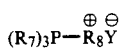

III $(R_7)_3\overset{\oplus}{P}-\overset{\ominus}{R_8Y}$ where R₈ is a saturated straight alkylene group with a chain length of two carbon atoms less than that of R₁, R₇ is aryl, and Y is halogen, to yield a compound of the formula

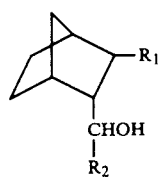

IV wherein R₁ and R₂ are as defined above.

23. A method of producing compounds of the formula

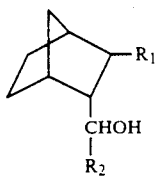

IV wherein R₁ is a group of the formula R'—COQ where R' is —(CH₂)$_j$— where j is an integer from 4 to 8; and COQ is carboxy, a physiologically acceptable carboxylate salt, a $C_1$-$C_5$ alkyl ester or CONHSO₂CH₃; and R₂ is selected from the group consisting of hydrogen, $C_{1-10}$ aliphatic hydrocarbon groups, and $C_{1-10}$ aliphatic hydrocarbon groups substituted by Ar, OAr and SAr, where Ar represents a phenyl, naphthyl, fluorenyl, dibenzocyclohexyl, dibenzocycloheptyl, pyridyl, benzthiazolyl, dihydrobenzthiazolyl, N-methyldihydrobenzthiazolyl, benzoxazolyl, dihydrobenzoxazolyl or N-methyldihydrobenzoxazolyl group or such a group substituted by one or more substituents selected from $C_{1-10}$ alkoxy, halogen, $C_{1-10}$ halogen-substituted alkyl, sulphamoyl, amino, hydroxyl, nitro and $C_{1-10}$ alkyl groups; which method comprises the steps of preparing the compound of formula IV as claimed in claim 47 by carrying out the steps (a) and (b) of claim 47 and then reducing the group R' in the compound of claim 47 to the group —(CH₂)$_j$— present in the compound of formula IV as defined above.

24. A method for producing compounds of the formula

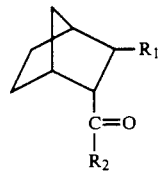

V wherein R₁ is a group of the formula R'—COQ in which R' is —CH₂—CH=CH—(CH₂)$_m$— where m is an integer of 1 to 5; and COQ is carboxy, a physiologically acceptable carboxylate salt, a $C_1$-$C_5$ alkyl ester or CONHSO₂CH₃; and R₂ is selected from the group consisting of hydrogen, $C_{1-10}$ aliphatic hydrocarbon groups, and $C_{1-10}$ aliphatic hydrocarbon groups substituted by Ar, OAr and SAr, where Ar represents a phenyl, naphthyl, fluorenyl, dibenzocyclohexyl, dibenzocycloheptyl, pyridyl, benzthiazolyl, dihydrobenzthiazolyl, N-methyldihydrobenzthiazolyl, benzoxazolyl, dihydrobenzoxazolyl or N-methyldihydrobenzoxazolyl group or such a group substituted by one or more substituents selected from $C_{1-10}$ alkoxy, halogen, $C_{1-10}$ halogen-substituted alkyl, sulphamoyl, amino, hydroxyl, nitro and $C_{1-10}$ alkyl groups; which method comprises the steps of:

(a) preparing a compound of the formula

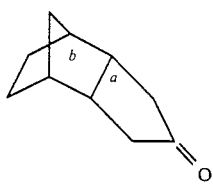 VI (b) reacting the compound of formula VI with a compound of the formula

R₂X wherein R₂ is as defined above and X is a halogen, such reaction taking place in the presence of a strong base;

(c) oxidizing, by peracid oxidation, the product of (b) to yield a product of formula VIII;

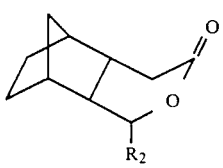 VIII (d) reducing the product of formula VIII to yield a compound of the formula

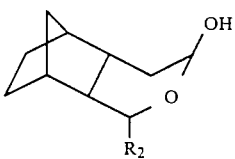 II wherein R₂ is as defined above;

(e) reacting the product of formula II with a compound of the formula $(R_7)_3\overset{\oplus}{P}-\overset{\ominus}{R_8Y}$  III wherein R₈ is a saturated straight chain alkylene group with a chain length of two carbon less than that of R₁, R₇ is aryl and Y is halogen, to yield a compound of the formula

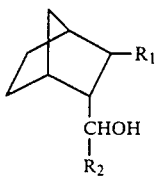 IV wherein R₁ and R₂ are as defined in claim 35; and (f) oxidizing the product of (e) to yield a compound of the formula V wherein R₁ and R₂ are as defined above.

25. A method for producing compounds of the formula

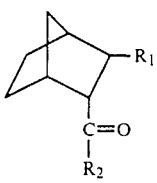 V wherein R₁ is a group of the formula R'COQ in which R' is —(CH₂)ⱼ— where j is an integer of 4 to 8; and COQ is carboxy, a physiologically acceptable carboxylate salt, a $C_{1-5}$ alkyl ester or CONHSO₂CH₃; and R₂ is selected from the group consisting of hydrogen, a $C_{1-10}$ aliphatic hydrocarbon groups, and $C_{1-10}$ aliphatic hydrocarbon groups substituted by Ar, OAr or SAr, where Ar represents a phenyl, naphthyl, fluorenyl, dibenzocyclohexyl, dibenzocycloheptyl, pyridyl, benzthiazolyl, dihydrobenzthiazolyl, N-methyldihydrobenzthiazolyl, benzoxazolyl, dihydrobenzoxazolyl, or N-methyldihydrobenzoxazolyl group or such a group substituted by one or more substituents selected from $C_{1-10}$ alkoxy, halogen, $C_{1-10}$ halogen-substituted alkyl, sulphamoyl, amino, hydroxyl, nitro and $C_{1-10}$ alkyl groups; the R' in the compound of formula IV then being reduced to the group —(CH₂)ⱼ— present in the compound of formula V, which method comprises the steps of:

(a) preparing a compound of the formula

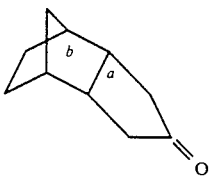 VI (b) reacting the compound of formula VI with a compound of the formula

R₂X wherein R₂ is as defined above and X is a halogen, such reaction taking place in the presence of a strong base;

(c) oxidizing, by peracid oxidation, the product of (b) to yield a product of formula VIII;

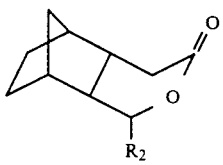 VIII (d) reducing the product of formula VIII to yield a compound of the formula

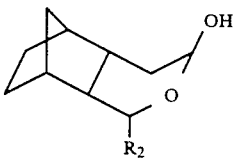 II wherein $R_2$ is as defined above;

(e) reacting the product of formula II with a compound of the formula

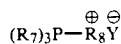  III wherein $R_8$ is a saturated straight chain alkylene group with a chain length of two carbon less than that of $R_1$, $R_7$ is aryl and Y is halogen, to yield a compound of the formula wherein $R_1$ is a group of the formula R'COQ in which R' is —$CH_2$—CH=CH—$(CH_2)_m$— where m is an integer from 1 to 5; and COQ and $R_2$ are as defined above; the group R' in the compound of formula IV then being reduced to the group —$(CH_2)_j$— present in the compound of formula V; and (f) oxidizing the product of (e) to yield a compound of the formula V wherein $R_1$ and $R_2$ are as defined above for the compound of formula V.

26. A method for producing compounds of the formula

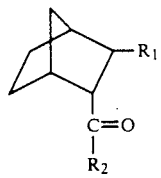 V where $R_1$ is a group of the formula R'-COQ where R' is —$(CH_2)_j$— where j is an integer from 4 to 8; and COQ is carboxy, a physiologically acceptable carboxylate salt, a $C_{1-5}$ alkyl ester or $CONHSO_2CH_3$; and $R_2$ is selected from the group consisting of hydrogen, a $C_{1-10}$ aliphatic hydrocarbon groups, and $C_{1-10}$ aliphatic hydrocarbon groups substituted by Ar, OAr or SAr, where Ar represents a phenyl, naphthyl, fluorenyl, dibenzocyclohexyl, dibenzocycloheptyl, pyridyl, benzthiazolyl, dihydrobenzthiazolyl, N-methyldihydrobenzthiazolyl, benzoxazolyl, dihydrobenzoxazolyl, or N-methyldihydrobenzoxazolyl group or such a group substituted by one or more substituents selected from $C_{1-10}$ alkoxy, halogen, $C_{1-10}$ halogen-substituted alkyl, sulphamoyl, amino, hydroxyl, nitro and $C_{1-10}$ alkyl groups; which method comprises the steps of preparing a compound of the formula V as claimed in claim 24 by carrying out the steps (a), (b), (c), (d), (e) and (f) of claim 24 and then reducing the group R' in the compound of claim 24 to the group —$(CH_2)_j$— present in the compound of formula V as defined above.

27. The method as claimed in claim 24, 25 or 26, in which the oxidizing agent used to produce the final product is a Jones reagent.

* * * * *

UNITED STATES PATENT AND TRADEMARK OFFICE
CERTIFICATE OF CORRECTION

PATENT NO. : 5,055,582
DATED : October 8, 1991
INVENTOR(S) : Garland et al

It is certified that error appears in the above-identified patent and that said Letters Patent is hereby corrected as shown below:

Column 1 line 11 change: "$1\alpha,\alpha$" to --$1\alpha,4a$--

Column 5 line 59 change: "Normal" to --normal--
    line 67 change: "pathoqenesis" to --pathogenesis--

Column 11 line 29 change: "($\pm$)octahydro-16O-methyl" to --($\pm$)octahydro-$1\alpha$-methyl-- lines 67-69 change: "($\pm$)7-[$3\beta$-(1R*-hydroxyethyl)-16O, $4\alpha$-bicyclo [2.2.1]hept-$2\alpha$-yl]-5Z-heptenoic acid" to --($\pm$)7-[$3\beta$-(1R*-hydroxyethyl)-$1\alpha,4\alpha$-bicyclo [2.2.1]hept-$2\beta$-yl]-5Z-heptenoic acid--

Column 16 line 68 change: "$R_3$ is a $C_1$ aliphatic" to --$R_3$ is a $C_{1-10}$ aliphatic--

Column 17 line 65 change: "=wherein" to --wherein--

Column 18 line 38 change: "$C_1$ alkoxy" to --$C_{1-10}$ alkoxy--
    line 40 change: "$C_1$alkyl" to --$C_{1-10}$ alkyl--.

Signed and Sealed this

Fifteenth Day of June, 1993

Attest:

MICHAEL K. KIRK

Attesting Officer    Acting Commissioner of Patents and Trademarks